(12) United States Patent
Kim et al.

(10) Patent No.: US 10,004,971 B2
(45) Date of Patent: Jun. 26, 2018

(54) PHYSICAL-FITNESS TEST SYSTEM USING ACCELERATION SENSOR

(71) Applicant: INDUSTRY-ACADEMIC COOPERATION FOUNDATION, YONSEI UNIVERSITY, Seoul (KR)

(72) Inventors: Youngho Kim, Gangwon-do (KR); Bora Ha, Gangwon-do (KR)

(73) Assignee: Yonsei University Wonju Industry-Academic Cooperation, Wonju-si, Kangwon-do (KR)

( * ) Notice: Subject to any disclaimer, the term of this patent is extended or adjusted under 35 U.S.C. 154(b) by 865 days.

(21) Appl. No.: 14/378,499

(22) PCT Filed: Jan. 10, 2013

(86) PCT No.: PCT/KR2013/000199
§ 371 (c)(1),
(2) Date: Aug. 13, 2014

(87) PCT Pub. No.: WO2013/122327
PCT Pub. Date: Aug. 22, 2013

(65) Prior Publication Data
US 2015/0039261 A1    Feb. 5, 2015

(30) Foreign Application Priority Data

Feb. 17, 2012 (KR) .................. 10-2012-0016515

(51) Int. Cl.
*A63B 24/00*    (2006.01)
*A63B 21/00*    (2006.01)
(Continued)

(52) U.S. Cl.
CPC .............. *A63B 71/06* (2013.01); *G01P 15/00* (2013.01); *G06Q 50/22* (2013.01)

(58) Field of Classification Search
CPC .......... G01P 15/00; G06Q 50/22; A61B 5/00; A61B 5/04; A61B 5/0404; A61B 5/0478; A61B 5/0408; A61B 5/11; A63B 71/06
See application file for complete search history.

(56) References Cited

U.S. PATENT DOCUMENTS

2006/0022833 A1 * 2/2006 Ferguson .............. A63F 13/211
340/573.1
2008/0015454 A1 * 1/2008 Gal .................... A41D 13/1281
600/509
(Continued)

FOREIGN PATENT DOCUMENTS

JP    2006-068300 A    3/2006
JP    2006-110180 A    4/2006
(Continued)

*Primary Examiner* — Patrick King
(74) *Attorney, Agent, or Firm* — Rabin & Berdo, P.C.

(57) ABSTRACT

The present invention relates to a fitness testing system using an acceleration sensor, of which a mobile device containing an acceleration sensor is attached to the body of the test subject and the test subject is induced to perform an exercise according to the fitness test instructions provided through the fitness testing process installed in a personal computer during which the acceleration signals are measured through RF communication for an output of the fitness test and assessment results. For this purpose, the present invention embodies a fitness measurement system consisting of an acceleration sensor device with a 3-axis acceleration sensor that is attached to the test subject to detect the 3-axis acceleration signals produced according to the test subject's movement and transmits the signals through RF communication; and an assessment and analysis unit that receives 3-axis acceleration signals from the acceleration sensor device through a host gateway and detects the maximum acceleration from the 3-axis acceleration signals received as the exercise intensity; wherein the execution processing unit (Continued)

of the assessment and analysis unit, in case the test items is "balance", receives the x-axis acceleration signals, which are related to the left and right movement of the test subject, and z-axis acceleration signals, which are related to the forward and backward movement, via the host gateway and detects the trajectory according to the input x- and z-axis acceleration signals and the maximum acceleration value according to the forward, backward, left and right movements.

6 Claims, 6 Drawing Sheets

(51) Int. Cl.
*A63B 71/06* (2006.01)
*G06Q 50/22* (2018.01)
*G01P 15/00* (2006.01)

(56) References Cited

U.S. PATENT DOCUMENTS

| | | | |
|---|---|---|---|
| 2008/0287770 A1* | 11/2008 | Kurzweil | A61B 5/0408 600/388 |
| 2009/0197749 A1* | 8/2009 | Merkel | A43B 3/00 482/148 |
| 2012/0188083 A1* | 7/2012 | Miller, II | A42B 3/046 340/573.1 |
| 2014/0062504 A1* | 3/2014 | Dawson | A61B 5/0408 324/658 |
| 2015/0105221 A1* | 4/2015 | Roush | G06Q 50/22 482/8 |

FOREIGN PATENT DOCUMENTS

| | | |
|---|---|---|
| JP | 2009-101108 A | 5/2009 |
| KR | 10-2011-0045658 A | 5/2011 |

\* cited by examiner

PHYSICAL-FITNESS TEST SYSTEM USING ACCELERATION SENSOR

TECHNICAL FIELD

The present invention relates to a fitness testing system using an acceleration sensor, and to be more specific, a fitness testing system using an acceleration sensor, which involves attaching a mobile device containing an acceleration sensor onto the body of the test subject, measuring the 3-axis acceleration signals as the test subject performs an exercise according to the fitness test guidance (instructions) provided through the fitness testing process installed on a personal computer, outputting the fitness test and assessment results and analyzing the ranking of the test subject among the subject group.

BACKGROUND ART

With the growing interest in health in the recent years, people have recognized the importance of choosing the right exercise for their individual characteristics based on an accurate understanding of their own fitness and recording, maintaining and managing the exercise routines. The incidence of obesity and adult diseases among elementary, middle and high school students has been increasing in the recent years. Accordingly, the relevant government agencies are conducting fitness tests and making multi-faceted efforts to expand their implementation as a means to encourage young people to exercise on a regular basis. For these reasons, an increasing number of instruments for fitness measurement and assessment such as the sidestep counter, height and weight measuring instrument, push-up counter, and jumping meter are being introduced at sports and health facilities.

However, the existing fitness measurement instruments provide insufficient information on the measuring method and it was difficult to accurately measure one's fitness in a quantitative manner. Also, the scope of their uses was limited to measurement for the purpose of assessment, and thus there were efforts to increase their utility for more effective and efficient utilization.

DISCLOSURE

Technical Problem

The technical issue to be resolved by this invention was to provide a fitness testing system with an acceleration sensor, which involves attaching a mobile device containing an acceleration sensor on the body of the test subject, measuring the 3-axis acceleration signals as the test subject performs an exercise according to the fitness test guidance (instructions) provided through the fitness testing process installed on a personal computer, outputting the fitness test and assessment results and analyzing the ranking of the test subject among the subject group.

Technical Solution

In order to resolve the technical issue, the present invention embodies a fitness measurement system, wherein an acceleration sensor device has a 3-axis acceleration sensor, measures the 3-axis acceleration signals according to the movements of the test subject on whom the acceleration sensor device is attached, and transmits the signals through RF communication; an assessment and analysis unit receives the 3-axis acceleration signals via a host gateway, and detects the maximum acceleration from the 3-axis acceleration signals as intensity of the exercise; and an acceleration sensor device comprises of a belt holder, a belt insertion unit and a belt. The belt holder has 'L' shape, and is located on the top and bottom parts at both left and right sides of the acceleration sensor device, provided that the ends are facing each other. The belt insertion unit has grooves that traverse the middle part of the front face of the acceleration sensor device for belt insertion. The belt is inserted from a belt holder on one side, passed through the belt insertion unit, pulled out from the belt holder on the other side, and wrapped around the waist of the test subject.

Also, the present invention embodies a fitness measurement system, wherein an acceleration sensor device has a 3-axis acceleration sensor, measures the 3-axis acceleration signals according to the movements of the test subject on whom the acceleration sensor device is attached, and transmits the signals through RF communication; an assessment and analysis unit, containing an execution processing unit, receives the 3-axis acceleration signals via a host gateway and detects the maximum acceleration as intensity of the exercise from the 3-axis acceleration; an execution processing unit of the assessment and analysis unit, in case the test is "balance", receives the x-axis acceleration signals, which are related to the left and right movement of the test subject and z-axis acceleration signals, which are related to the forward and backward movement of the test subject, via a host gateway, and measuring the trajectory according to the x-axis acceleration signals and z-axis acceleration signals, and detecting the maximum acceleration of each of the forward, backward, left and right movements of the test subject.

Also, the present invention embodies a fitness measurement system, wherein an acceleration sensor device has a 3-axis acceleration sensor, measures the 3-axis acceleration signals according to the movements of the test subject on whom the acceleration sensor device is attached, and transmits the signals through RF communication; an assessment and analysis unit contains an execution processing unit that receives the 3-axis acceleration signals via a host gateway and detects the maximum acceleration as intensity of the exercise from the 3-axis acceleration; an execution processing unit of the assessment and analysis unit, in case the test items is "jumping", receives the y-axis acceleration signals, which are related to the up and down movements of the test subject, via a host gateway, detects the maximum acceleration signal among the y-axis acceleration signals, and measures the jumping duration and the jumping height.

Also, the present invention embodies a fitness measurement system, wherein an acceleration sensor device has a 3-axis acceleration sensor, measures the 3-axis acceleration signals according to the movements of the test subject on whom the acceleration sensor device is attached, and transmits the signals through RF communication; an assessment and analysis unit contains an execution processing unit that receives the 3-axis acceleration signals via a host gateway and detects the maximum acceleration as intensity of the exercise from the 3-axis acceleration; and an execution processing unit of the assessment and analysis unit comprises of a fitness and physical balance assessment unit and a measurement result analysis and management unit. The fitness and physical balance assessment unit outputs the images on the monitor to provide guidance for the selected test item among "balance", "jumping", "spot running", and "push-ups", and receives the 3-axis acceleration signals from the acceleration sensor device attached to the test subject, and detects the maximum acceleration and repetition count as the test results, and saves the test results in the database according to the test subject and the test item. The measurement result analysis and management unit, reads the assessment results of the selected test item from the database, and outputs the analysis results including the rankings of the test subjects.

It is comprised of a groove in the belt insertion unit wherein there is a DIP (Dual In-line Package) switch unit, and an RF channel selector, which can arbitrarily set the identification number of an acceleration sensor device for RF communication purposes by adjusting the DIP switches inside the DIP switch unit.

The said host gateway receives 3-axis acceleration signals through RF communication from the acceleration sensor device and transmits it to the assessment and analysis unit through an Ethernet interface unit.

The execution processing unit of the assessment and analysis unit detects the maximum acceleration of the y-axis acceleration signals and the repetition count of the spot running, in spot running tests, and detects the maximum acceleration of the y-axis acceleration signals and the repetition count of the push-ups in push-up tests.

The execution processing unit of the assessment and analysis unit outputs the images on the monitor to provide sequential guidance for the test items including the balance test, the jumping test, the spot running test, and the push-ups test, receives the 3-axis acceleration signals from the acceleration sensor device attached to the test subject, detects the maximum acceleration and repetition count as the test results, and saves the test results in the database according to the test subject and the test item. Also the execution processing unit of the assessment and analysis unit saves the ID, name, gender and birthdate of each test subject before the test.

The execution processing unit of the assessment and analysis unit outputs the results of each test item based on a comparison with the results of other test subjects.

The execution processing unit of the assessment and analysis unit, in case of a jumping test, detects the time point at which the value of the y-axis acceleration signal exceeds the jumping start threshold value as the jumping start time, and detects the time point at which the value of the y-axis acceleration signal falls below the jumping end threshold value after the jumping start time as the jumping end time, and detects the time between the jumping start time and the jumping end time as the jumping duration.

The execution processing unit of the assessment and analysis unit, in case of a jumping test, detects the acceleration value in the middle point between the jumping start time and the jumping end time, as mid-point acceleration value, and determines the jumping height by subtracting the jumping start time from the jumping end time, dividing the subtracted result value by 2, squaring the divided result value, and multiplying the squared result value by the mid-point acceleration value.

The execution processing unit of the assessment and analysis unit, in case of a spot running test, detects the time point at which the value of the y-axis acceleration signal exceeds the spot running start threshold value as the spot running start time of one foot, and detects the time point at which the value of the y-axis acceleration signal falls below the spot jumping end threshold value after the spot running start time of one foot, as the spot running end time of one foot, and detects the next time point at which the value of the y-axis acceleration signal exceeds the spot running start threshold value as the spot running start time of the other foot, and detects the time point at which the value of the y-axis acceleration signal falls below the spot running end threshold value after the spot running start time of the other foot as the spot running end time of the other foot. When the spot running start time of one foot and the spot running end time of the other foot are detected, it is counted as one repetition.

The execution processing unit of the assessment and analysis unit, in case of a push-up test, detects the time point at which the value of the y-axis acceleration signal falls below the push-up start threshold value as the push-up start time and the time point at which the value of the y-axis acceleration signal exceeds the push-up end threshold value after the push-up start time as the push-up end time, and counts as one repetition when the push-up start time and the push-up end time are detected.

Advantageous Effects

The fitness testing system using an acceleration sensor of the present invention allows a quantitative assessment of the fitness and physical balance of the test subject based on an analysis of the repetition and intensity of the exercise by measuring the subject's movement through RF communication using an acceleration sensor device attached to the subject according to the selected test item. Thus, it can be used by an institution specializing in fitness promotion and rehabilitation to perform fitness tests and assessments on seniors, overweight or obese children and cerebroneural disease patients, etc. with more convenience.

Also, as the present invention only uses an acceleration sensor, it generally has a simple structure, thus is an economical, scientific and quantitative invention.

In addition, the present invention makes it possible to measure the test subject's movements through RF communication and perform a quantitative assessment of his/her fitness and the physical balance based on the analysis of the results. Thus, it may be applied in combination with smart devices and to movement-recognition game devices, etc. in the future.

BEST MODE

The interpretation of the terms and words used in this specification and the scope of claims should not be limited to their common usage and/or definitions in the dictionary. Instead, they should be interpreted according to the technical ideas and concepts of the present invention, predicated on the principle that the inventor can define the concept of the terms used appropriately in order to explain his/her invention as best as possible. Thus, the implementation cases explained in the specification and the structures indicated in the figures are merely the most desirable cases of implementing this invention, and one must understand that there are various other equivalent structures and variations that can be used as alternatives.

Figure 1:
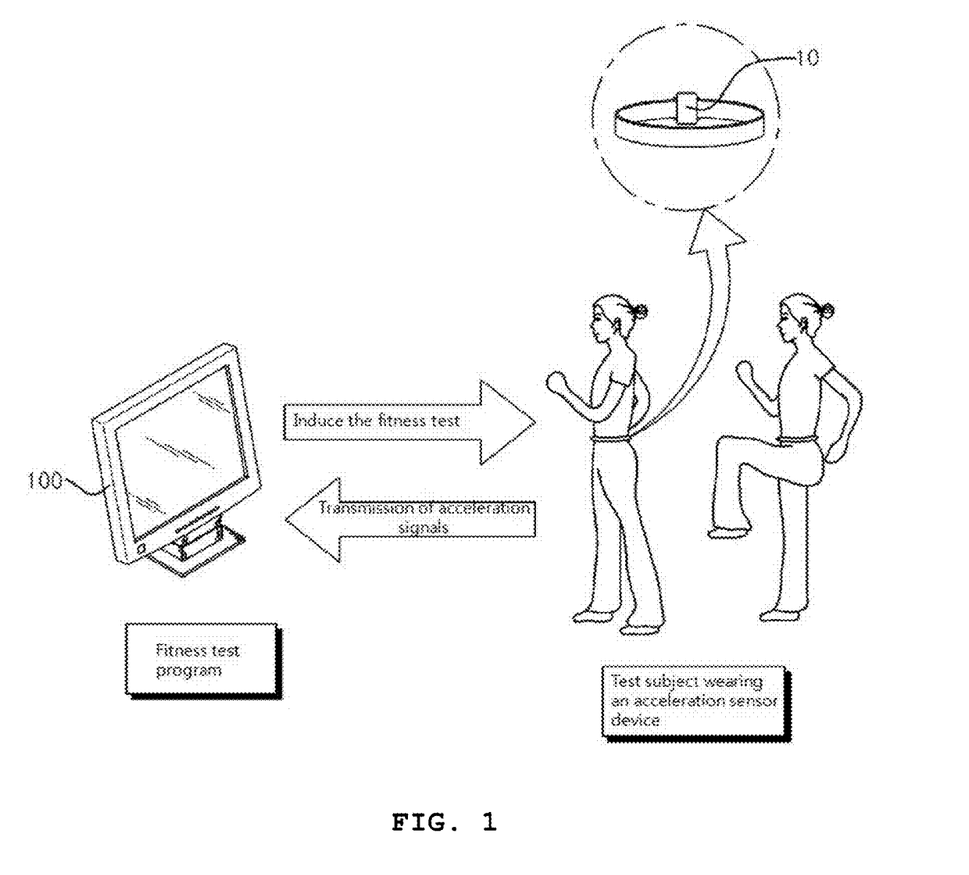
FIG. 1 is a conceptual diagram of a fitness testing system using an acceleration sensor in the present invention.
Figure 2:
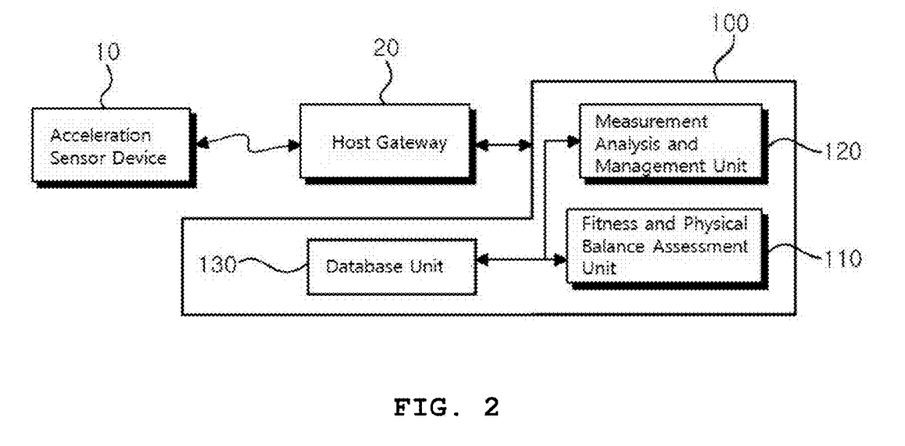
FIG. 2 is a block diagram of the composition of a fitness testing system using an acceleration sensor in the present invention.

FIG. 1 is a conceptual diagram of the present invention, which is a fitness testing system using an acceleration sensor, while FIG. 2 is a block diagram of composition of the fitness testing system. The structure of the present invention can largely be divided into a portable acceleration sensor device (10), a host gateway (20) for RF communication, and an assessment and analysis unit (100) embedded with fitness testing processes.

The acceleration sensor device (10), designed to engage in RF communication with the assessment and analysis unit (100) through the host gateway (20), is attached to the body of a test subject to measure the acceleration signals according to the subject's movement to be transmitted through RF communication. The acceleration sensor device (10) may have a unique identification number for the purpose of device identification.

The acceleration sensor device (10) is designed to communicate wirelessly with the assessment and analysis unit (100) through the host gateway (20). The acceleration sensor device (10) is attached to the body of a test subject, and measure the acceleration signals according to the subject's movement, and is transmitted the acceleration signals through RF communication. The acceleration sensor device (10) may have a unique identification number for the purpose of device identification.

The host gateway (20) transmits the wired or RF communication signals between the acceleration sensor device (10) and assessment and analysis unit (100).

The assessment and analysis unit (100) is comprised of a measurement analysis and management unit (120), a fitness and physical balance assessment unit (110), and a database unit (130). It is embedded with fitness test management processes to induce the movement in a test subject attached with an acceleration sensor device (10), and receives the acceleration signals that are through RF communication transmitted from the acceleration sensor device (10) via the host gateway (20) for processing and analysis. Based on the analysis results, it assesses the subject's fitness and physical balance to output the fitness test and assessment results with the subject's information. The fitness test management processes can be designed to allow step-by-step measurements of multiple test items that were determined in advance and such test items are "balance," "jumping," "spot running" and "push-up." The assessment and analysis unit (100) may consist of a computer.

In the balance test, the test subject extends his/her arms toward the sides and lifts one of the legs. Data on the left-and-right and forward-and-backward movements, i.e. the maximum left, right, forward and backward accelerations, are detected.

In the jumping test, the test subject jumps vertically from the spot where he or she is standing. The maximum acceleration of the up-and-down movements as well as the jumping duration and height are detected.

In the spot running test, the test subject runs on the spot. The number of times both feet are moved in a running motion, i.e. the repetition count of running on the spot, and the maximum acceleration of the up-and-down movements are detected.

In the push-up test, the test subject supports his or her body weight using both arms on a prone position and raises and lowers his/her body by bending and extending the arms. The maximum acceleration of the up-and-down movements and the repetition count of the push-ups are detected.

The fitness and physical balance assessment unit (110) provides guidance (instructions) on the test items (balance, jumping, spot running and push-up) according to the fitness testing processes, and receives the acceleration signals from the acceleration sensor device (10) attached to the test subject. The acceleration signals are then saved in the database unit according to the test subject. The maximum acceleration and repetition count of the exercise, etc. are detected and the fitness and physical balance of the subject are assessed and outputted accordingly and are saved in the database unit (130) according to the subject at the same time.

The measurement analysis and management unit (120) is used to register each of the test subjects prior to testing, and at the time of the registration, the ID, name, gender and birthdate of each subject are saved. Also, this unit is used to analyze and management the test data saved in the fitness and physical balance assessment unit (110) according to the subject. It calculates the mean value of the balance, jumping, spot running and push-up test results for the test group and determines the ranking of each subject in the group to be outputted and saved in the database unit (130). In addition, the result of each test item is compared to that of another test subject designated by the test subject in question.

The database unit (130) saves the personal information (ID, name, gender and birthdate) of each test subject, unprocessed data files of the acceleration signals obtained for each test item, the test results such as the repetition count and maximum acceleration obtained by the fitness and physical balance assessment unit (110), and the analysis results obtained by the measurement analysis and management unit (120) such as the subject rankings and mean values, etc., as per the test subject.

Figure 3:
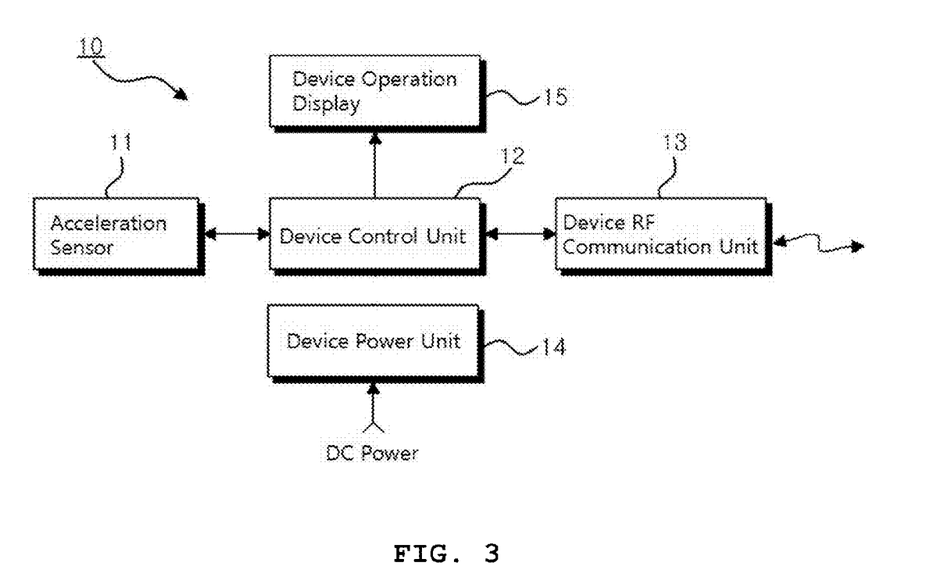
FIG. 3 is a block diagram, showing more details of the acceleration sensor device shown in FIG. 2.

FIG. 3 is a block diagram, showing more details of the acceleration sensor device shown in FIG. 2. The acceleration sensor device (10) is comprised of an acceleration sensor (11), device control unit (12), device RF communication unit (13), device power unit (14), and device operation display (15).

The acceleration sensor (11) is 3-axis acceleration sensor, which measures the acceleration signals from the x-, y- and z-axes according to the movements of the test subject and sends the signals to the control unit (12). This is embedded in the acceleration sensor device (10).

The device control unit (12) contains a signal preprocessing unit (not shown in the figures) for noise removal and amplification. The device control unit (12) also operates the acceleration sensor (11), and receives the 3-axis (x-, y- and z-axes) acceleration signals from the acceleration sensor (11). The 3-axis acceleration signal passing through the signal preprocessing unit is converted to be transmitted through RF communication.

Additionally, the control unit (12) is responsible for the overall control of the acceleration sensor device (10), controlling the operations of each part of the acceleration sensor device (10) and the display that shows their operating status.

The device control unit (12) may be equipped with an identification number setting switch, to arbitrarily set a unique identification number for the acceleration sensor device (10), and in this case, a unique identification number may be given to the device control unit (12) by the identification number setting switch. The control unit (12) may also have a separate power switch to control the overall operations of the device and this switch will allow the device operations to be controlled manually.

The device RF communication unit (13) receives the acceleration signals that were converted for RF transmission from the control unit (12) and sends the signals to the host gateway (20) in real time.

The device power unit (14) supplies power to each part of the acceleration sensor device (10), and contains a power terminal through which external direct current power can be supplied for charging of the battery.

The device operation display (15) is turned on by the control unit (12) and displays the operation status of each part of the acceleration sensor device such as the operation status of the RF communication unit, power supply status of the power unit, etc. The device operation display (15) may be comprised of 3 LED displays that show the power supply, battery and communication status.

Figure 4:
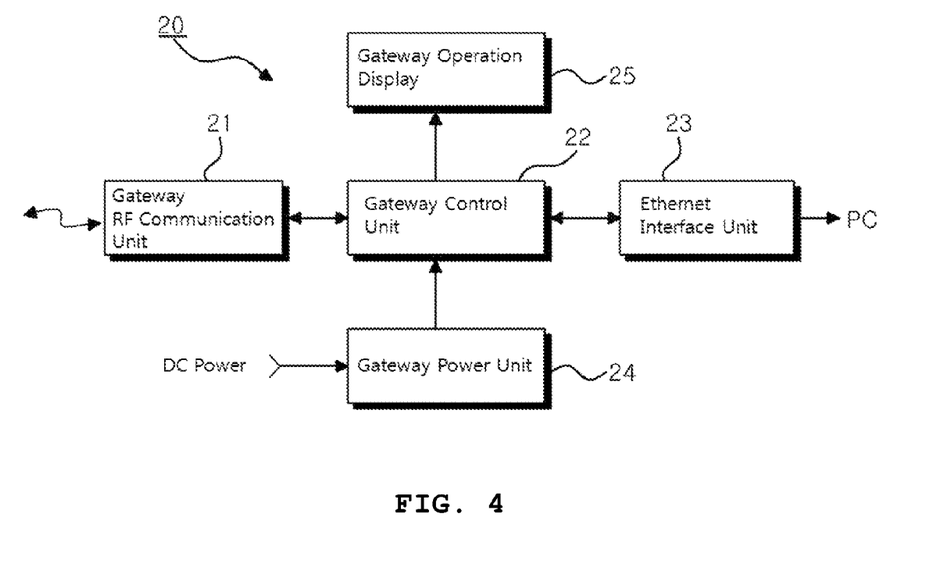
FIG. 4 is a block diagram, showing more details of the host gateway shown in FIG. 2.

FIG. 4 is a block diagram, showing more details of the host gateway shown in FIG. 2. The host gateway (20) is comprised of a gateway RF communication unit (21), gateway control unit (22), Ethernet interface unit (23), gateway power unit (24), and gateway operation display unit (25).

The gateway RF communication unit (21) of the gateway is a means to transmit signals with the acceleration sensor device (10) through RF communication. It receives the 3-axis acceleration signals according to the subject's movements from the acceleration sensor device (10) and sends them to the gateway control unit (22).

The gateway control unit (22) receives the 3-axis acceleration signals from the acceleration sensor device (10) via the gateway RF communication unit (21) and sends them to the assessment and analysis unit (100) via the Ethernet interface unit (23). Also, the gateway control unit (22) is responsible for the overall control of the host gateway (20), controlling the operations of each part of the host gateway (20) and the display that shows their operation status.

The Ethernet interface unit (23) sends the 3-axis acceleration signals transmitted from the gateway control unit (22) to the assessment and analysis unit (100) installed with fitness testing processes.

The gateway power unit (24) supplies power to each part of the host gateway (20), and contains a power terminal through which external direct current power can be supplied for charging of the battery.

The gateway operation display (25) operates by the gateway control unit (22) and displays the operation status of each part of the gateway. The operation display (25) may be comprised of 2 LED displays that show the power and communication status.

Figure 5:
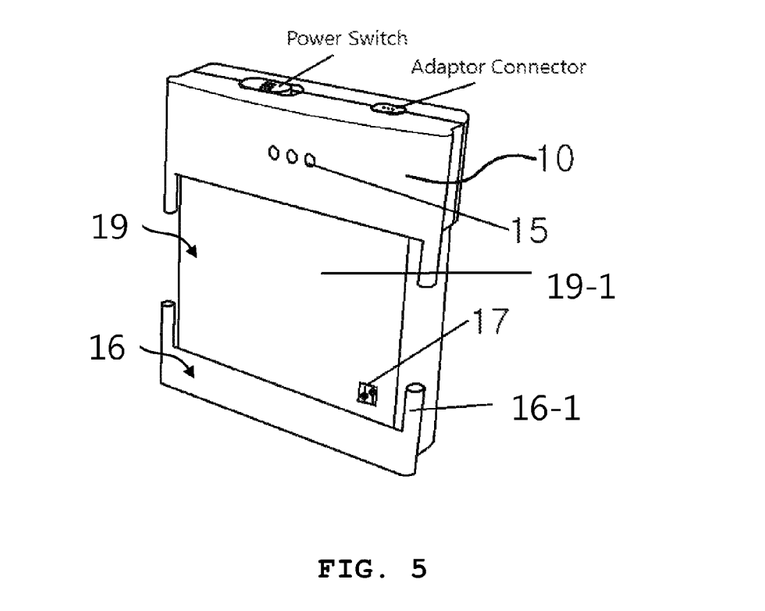
FIG. 5 shows an example of the acceleration sensor device shown in FIG. 2.
Figure 6:
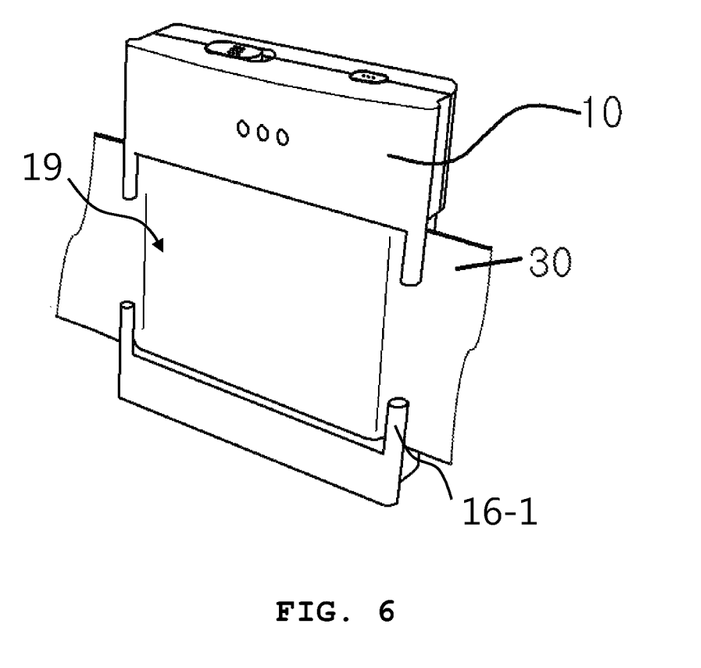
FIG. 6 is an operating status diagram of the acceleration sensor device shown in FIG. 5.

FIG. 5 shows an example of the acceleration sensor device shown in FIG. 2. FIG. 6 is an operating status diagram of the acceleration sensor device shown in FIG. 5.

The acceleration sensor device (10) is comprised of a belt insertion unit (19), in which the belt (30) for fixing the acceleration sensor device (10) on the body of the test subject (e.g. the waist) is inserted, a belt holder (16) for fixing the belt (30). Also the acceleration sensor device (10) has an RF channel selector (17) comprised of a DIP switch in the belt insertion unit (19). On one side of the acceleration sensor device (10), there is a power switch and an adaptor connector.

The belt holder (16) in is an 'L' shape. To be more specific, the belt holder (16) comprises strips (16-1) that are perpendicular to each other. The belt holder (16) is placed on the top and bottom parts at both right and left sides of the acceleration sensor device (10). The ends of the belt holder (16) located on the top and bottom parts at both right and left sides of the acceleration sensor device (10) face each other.

The belt insertion unit (19) has a groove (19-1) that traverses the middle part of the front face of the acceleration sensor device for belt insertion.

The belt (30) are inserted from a belt holder (16) on one side, passed through the belt insertion unit, pulled out from a belt holder (16) on the other side, and wrapped around the waist of test subject.

The RF channel selector (17) is an identification number setting switch for the acceleration sensor device (10). There is a groove in the belt insertion unit (19), in which there is a DIP switch unit, and the DIP switches are adjusted to set the identification number of the acceleration sensor device (10).

Figure 7:
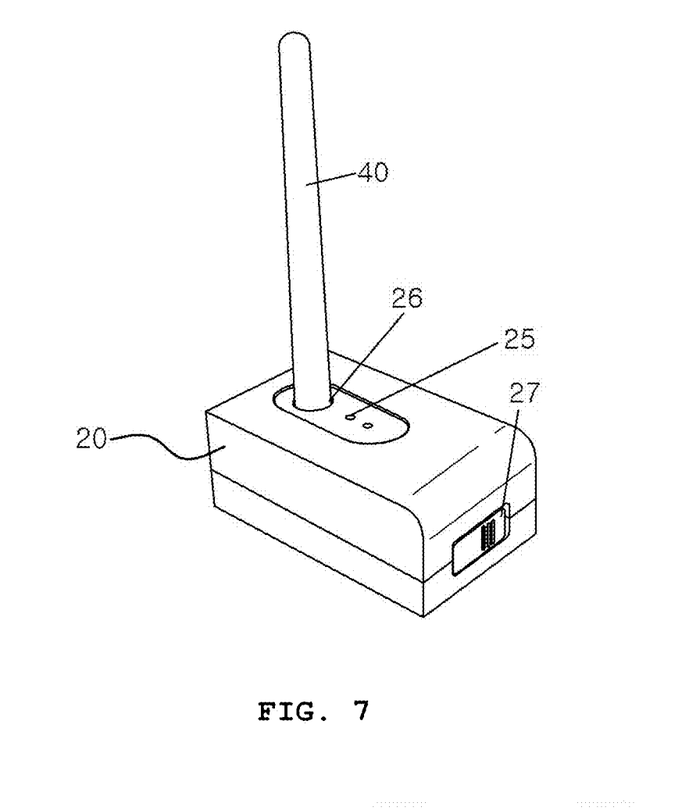
FIG. 7 shows an example of the host gateway shown in FIG. 2.

FIG. 7 shows an example of the host gateway shown in FIG. 2.

The host gateway (20) contains an antenna connector (26) and a gateway operation display (25) in the upper part and a gateway power switch (27) on one side.

Figure 8:
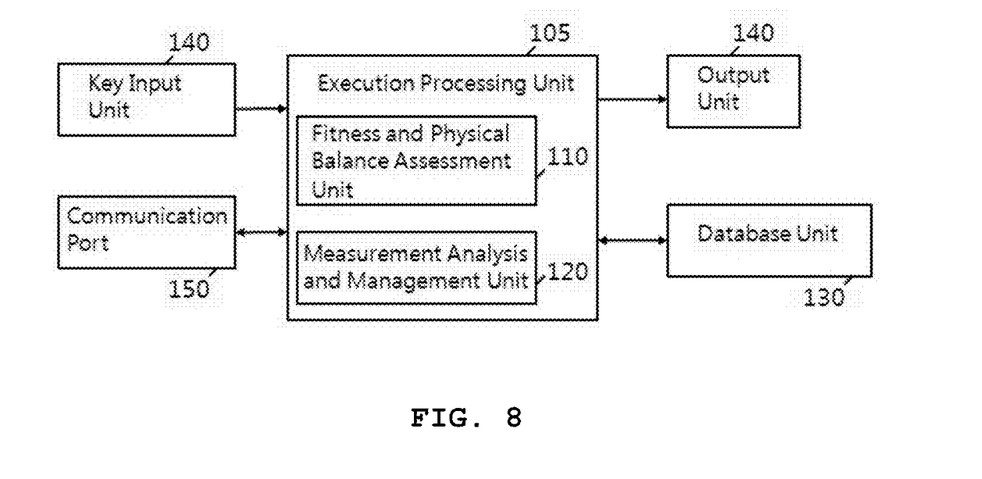
FIG. 8 is a block diagram, showing the composition of the assessment and analysis unit shown in FIG. 2.

FIG. 8 is a block diagram, showing the composition of the assessment and analysis unit shown in FIG. 2. It is comprised of a execution processing unit (arithmetic processing unit) (105), a database unit (130), a key input unit (140), a communication port (150), and an output unit (160).

The execution processing unit (105), consisting of a microprocessor, is responsible for the overall control of the assessment and analysis unit (100). It is comprised of a measurement analysis and management unit (120) and fitness and physical balance assessment unit (110), and deciphers and analyzes the test data based on the 3-axis acceleration signals transmitted from the host gateway (20).

The fitness and physical balance assessment unit (110) outputs the images or the sounds with output unit (160) to provide explanations about test method of the test item (balance, jumping, spot running or push-up), or to provide the guidance (instructions) given for the test item. And then, the test subject attached the acceleration sensor device (10), performs the exercise of the test item according to the images or the sounds. And, the fitness and physical balance assessment unit (110) receives the 3-axis acceleration signals from the acceleration sensor device (10) attached to the test subject, and detects the maximum acceleration and repetition count, etc., according to the subject's movements.

For instance, in case the test item is "balance," the x- and z-axis acceleration signals (left-and-right and forward-and-backward movement data) of the test subject are received and the trajectory based on the acceleration signals as well as the maximum acceleration values for the left-and-right and forward-and-backward movements, i.e. the maximum intensity value (unit: $cm/s^2$) are detected.

In case the test item is "jumping", the fitness and physical balance assessment unit (110) receives the y-axis acceleration signals (up-and-down movement data) of the test subject from the acceleration sensor device (10), and detects the maximum y-axis acceleration of the y-axis acceleration signals, and detects the jumping duration and the jumping height. The jumping duration refers to the duration between the time point at which the subject's feet were lifted off the ground and the time point at which they touched the ground again. The fitness and physical balance assessment unit (110) detects the time point at which the value of the y-axis acceleration signal exceeds the jumping start threshold value as the jumping start time, and detects the time point at which the value of the y-axis acceleration signal falls below the jumping end threshold value after the jumping start time as the jumping end time, and detects the time between the jumping start time and the jumping end time as the jumping duration. The height of the jump, i.e. the maximum height of the jump, is the acceleration value in the middle point between the jumping start time and the jumping end time, as mid-point acceleration value. The fitness and physical balance assessment unit (110) determines the jumping height by subtracting the jumping start time from the jumping end time, dividing the subtracted result value by 2, squaring the divided result value, and multiplying the squared result value by the mid-point acceleration value.

In case the test item is "spot running", the maximum acceleration (i.e. the maximum y-axis acceleration) among the y-axis acceleration signals (up-and-down movement data) and the repetition count of the spot running are measured. In this case, one repetition involves raising one of the feet off the ground and placing it back on the ground and raising the other feet off the ground and placing it back on the ground. To be more specific, the fitness and physical balance assessment unit (110) detects the time point at which the value of the y-axis acceleration signal exceeds the spot running start threshold value as the spot running start time of one foot, and detects the time point at which the value of the y-axis acceleration signal falls below the spot jumping end threshold value after the spot running start time of one foot as the spot running end time of one foot. Then it detects the next time point at which the value of the y-axis acceleration signal exceeds the spot running start threshold value as the spot running start time of the other foot, and detects the time point at which the value of the y-axis acceleration signal falls below the spot running end threshold value after the spot running start time of the other foot as the spot running end time of the other foot. When the spot running start time of one foot and the spot running end time of the other foot are detected, it will be counted as one repetition.

In case the test item is "push-up", the maximum acceleration (i.e. the maximum y-axis acceleration) among the y-axis acceleration signals (up-and-down movement data) and the repetition count of the push-ups are measured. In this case, The fitness and physical balance assessment unit (110) detects the time point at which the value of the y-axis acceleration signal falls below the push-up start threshold value as the push-up start time, and detects the time point at which the value of the y-axis acceleration signal exceeds the push-up end threshold value after the push-up start time as the push-up end time. When the push-up start time and the push-up end time are detected, it will be counted as one repetition.

The jumping start, jumping end, spot running start, stop running end, push-up start and push-up end threshold values may have already been saved before the device was shipped out from the factory, or the they may have been set by taking a prescribed percentage (e.g. 10~30% of the mean values) of the mean values of the jumping, spot running and push-ups performed by the test subject using the acceleration sensor device (10).

The measurement analysis and management unit (120) is used to register each of the test subjects prior to testing, and at the time of the registration, the ID, name, gender and birthdate of each subject are saved. Also, this unit is used to analyze and management the test data saved in the fitness and physical balance assessment unit (110) according to the subject. It calculates the mean value of the balance, jumping, spot running and push-up test results for the test group and determines the ranking of each subject in the group to be outputted and saved in the database unit (130). In addition, the result of each test item is compared to that of another test subject designated by the test subject in question.

The database unit (130) saves the personal information (ID, name, gender and birthdate) of each test subject, unprocessed data files of the acceleration signals obtained for each test item, the test results such as the repetition count and maximum acceleration obtained by the fitness and physical balance assessment unit (110), and the analysis results obtained by the measurement analysis and management unit (120) such as the subject rankings and mean values, etc. In addition, the jumping start, jumping end, spot running start, stop running end, push-up start and push-up end threshold values are saved in this unit.

The key input unit (140) is used to enter the information of the test subject or set the function, and it may be comprised of a keyboard or a user interface unit. The setup modes include a general testing mode and a rapid testing mode; in the general testing mode, the test designated by the user is conducted, while in the rapid testing mode, all the tests, i.e. the balance, jumping, spot running and push-up tests, are conducted step by step.

The communication port (150) is connected to the Ethernet interface unit (23) of the host gateway (20) for communication.

The output unit (160) is comprised of a printer, a monitor or speakers, etc. to output the test results and provide guidance (instructions) on the test items.

Figure 9:
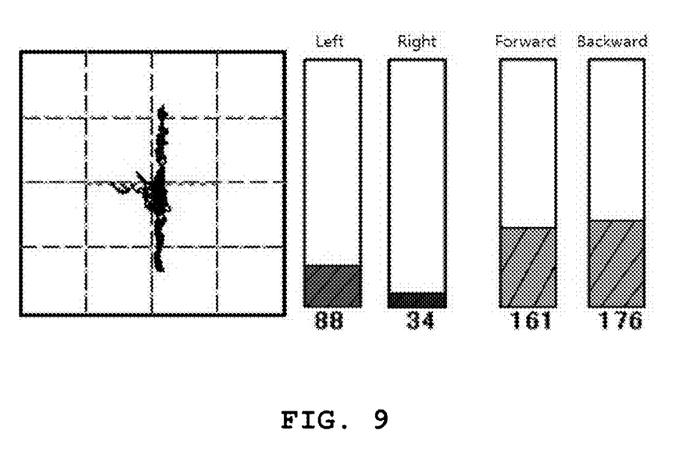
FIG. 9 shows an example of the result of performing a balance test, using the fitness testing system of the present invention.
Figure 10:
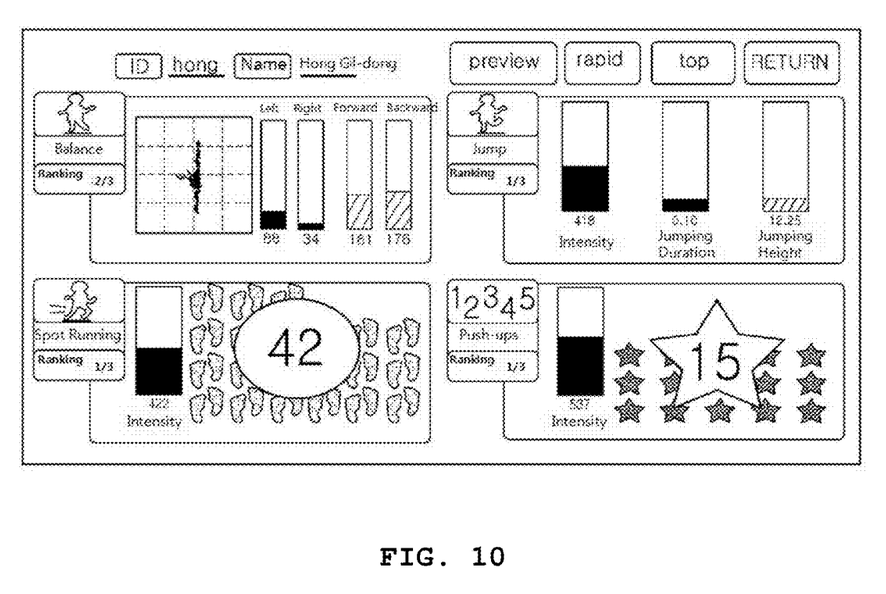
FIG. 10 shows an example of the result of performing all of the 4 test items, using the fitness testing system of the present invention.

FIG. 9 shows an example of the result of performing a balance test, using the fitness testing system of the present invention. FIG. 10 shows an example of the result that performs all of the 4 test items, using the fitness testing system of the present invention.

FIG. 9 and FIG. 10 present the results shown on the output unit (160). FIG. 9 shows a graph of the trajectory determined according to the x-axis and z-axis acceleration signals for a balance test as well as the maximum acceleration value (maximum intensity value) of each of the left, the right, the forward and the backward movements. On the other hand, FIG. 10 shows the results of the four tests, i.e. the balance, jumping, spot running and push-up tests, and the subject ranking in the group.

For the jumping test, the maximum acceleration (intensity), jumping duration and jump height are determined. For the spot running test, the maximum acceleration (intensity) and the repetition count of spot running are determined. For the push-up test, the maximum acceleration (intensity) and the repetition count of push-ups are determined.

As shown in the above paragraphs, according to the present invention, the test subject can measure his or her fitness based on the guidelines on the test items for fitness measurement provided through the fitness testing processes, allowing him/her to measure his/her fitness according to an accurate measurement method. Also, it saves the measurement and analysis results for a quantitative analysis, if necessary. Because the data on multiple subjects can be saved and managed, a comparative analysis is also possible.

An embodiment of the present invention was explained through limited examples and drawings, but the present invention is not limited to the above examples as it can be modified and changed by anyone with the common knowledge in the field of the present invention. Thus, the ideas of the present invention should be understood based on the scope of the claims indicated below, and all the equal and equivalent modifications fall within the scope of the ideas behind the present invention.

INDUSTRIAL APPLICABILITY

The present invention embodies the fitness testing system using an acceleration sensor which is applicable to the fitness tests performed at schools, hospitals, etc., and may be applied in combination with smart devices and to movement-recognition game devices, etc. in the future.

What is claimed is:

1. A fitness measurement system, comprising:
an acceleration sensor device having a 3-axis acceleration sensor and configured to measure 3-axis acceleration signals according to the movements of a test subject on whom the acceleration sensor device is attached and transmit the signals through RF communication, the acceleration sensor device including a belt insertion unit to support a belt;
an RF channel selector configured to arbitrarily set an identification number of the acceleration sensor device for the RF communication; and
an assessment and analysis unit configured to receive the 3-axis acceleration signals via a host gateway and detect a maximum acceleration from the 3-axis acceleration signals as an intensity of the exercise,
wherein the belt insertion unit of the acceleration sensor device includes
a groove formed across a middle part of a front side of the acceleration sensor device with a predetermined width and depth, and
a belt holder including four strips disposed around four corners of the groove, respectively, wherein each of the four strips extends over the groove from the acceleration sensor device such that an outer surface of said each of the four strips is on the same plane with the front side of the acceleration sensor device, and an inner surface of said each of the four strips is apart from a surface of the groove with a gap through which a belt passes,
wherein the RF channel selector is disposed on the surface of the groove, and
wherein the belt is configured to attach the acceleration sensor device to the test subject.

2. The fitness testing system according to claim 1, wherein the RF channel selector is a DIP (Dual In-line Package) switch type.

3. The fitness testing system according to claim 1, wherein the host gateway receives the 3-axis acceleration signals through the RF communication from the acceleration sensor device and transmits it to the assessment and analysis unit through an Ethernet interface unit.

4. The fitness testing system according to claim 1, wherein the assessment and analysis unit,
in case of balance test, receives x-axis acceleration signals which are related to the left and right movements of the test subject, and z-axis acceleration signals which are related to the forward and backward movements of the test subject, via the host gateway, and measures a trajectory according to the x-axis acceleration and z-axis acceleration signals, and detectives a maximum acceleration of each of the forward, backward, left and right movements of the test subject;
in case of a jumping test, receives y-axis acceleration signals which are related to the up and down movements of the test subject, via the host gateway, and detectives a maximum acceleration among the y-axis acceleration signals, and measures a jumping duration and a jumping height;
in case of a spot running test, detects the maximum acceleration among the y-axis acceleration signals, and a repetition count of a spot running; and
in case of a push-up test, detects the maximum acceleration among the y-axis acceleration signals, and a repetition count of push-ups.

5. The fitness testing system according to claim 1, wherein the assessment and analysis unit outputs images on a monitor to provide guidance in sequence for the tests including the balance test, the jumping test, the spot running test, and the push-up test, receives the x-axis, y-axis and z-axis acceleration signals from the acceleration sensor device attached to the test subject, detects the maximum acceleration and repetition count as test results, and saves the test results in a database according to the test subject and the tests.

6. The fitness testing system according to claim 1, wherein the assessment and analysis unit saves an ID, a name, a gender and a birthdate of each test subject before the test.

* * * * *